(12) United States Patent
Lulla et al.

(10) Patent No.: US 8,168,620 B2
(45) Date of Patent: May 1, 2012

(54) COMBINATION OF AZELASTINE AND STEROIDS

(75) Inventors: Amar Lulla, Mumbai (IN); Geena Malhotra, Mumbai (IN)

(73) Assignee: CIPLA Limited, Mumbai (IN)

( * ) Notice: Subject to any disclaimer, the term of this patent is extended or adjusted under 35 U.S.C. 154(b) by 987 days.

(21) Appl. No.: 10/518,016

(22) PCT Filed: Jun. 13, 2003

(86) PCT No.: PCT/GB03/02557
§ 371 (c)(1),
(2), (4) Date: Jul. 6, 2005

(87) PCT Pub. No.: WO03/105856
PCT Pub. Date: Dec. 24, 2003

(65) Prior Publication Data
US 2006/0025391 A1    Feb. 2, 2006

(30) Foreign Application Priority Data

Jun. 14, 2002 (GB) .................................. 0213739.6

(51) Int. Cl.
*A01N 45/00* (2006.01)
*A61K 31/56* (2006.01)
*A61K 31/55* (2006.01)
*A61K 31/57* (2006.01)
*A61K 31/58* (2006.01)
*A61K 9/00* (2006.01)
*A61P 37/08* (2006.01)
*A61P 27/14* (2006.01)
*A61P 11/06* (2006.01)

(52) U.S. Cl. .................................................... 514/171
(58) Field of Classification Search ................. 514/171
See application file for complete search history.

(56) References Cited

U.S. PATENT DOCUMENTS

| | | | |
|---|---|---|---|
| 2,837,464 A | 6/1958 | Nobile | |
| 3,067,197 A | 12/1962 | Agnello et al. | |
| 3,312,590 A | 4/1967 | Elks et al. | |
| 3,506,694 A | 4/1970 | Oxley | |
| 3,557,162 A | 1/1971 | Voorschoten et al. | |
| 3,639,434 A | 2/1972 | Oxley et al. | |
| 3,755,302 A | 8/1973 | Ercoli et al. | |
| 3,828,080 A | 8/1974 | May et al. | |
| 3,856,828 A | 12/1974 | Phillipps et al. | |
| 3,891,631 A | 6/1975 | Phillipps et al. | |
| 3,981,894 A | 9/1976 | Phillipps et al. | |
| 3,989,686 A | 11/1976 | Phillipps et al. | |
| 4,093,721 A | 6/1978 | Phillipps et al. | |
| 4,113,680 A | 9/1978 | Kamano et al. | |
| 4,187,301 A | 2/1980 | Edwards | |
| 4,188,385 A | 2/1980 | Edwards | |
| 4,198,403 A | 4/1980 | Alvarez | |
| 4,221,787 A | 9/1980 | Bodor et al. | |
| 4,261,984 A | 4/1981 | Alvarez | |
| 4,263,289 A | 4/1981 | Edwards | |
| 4,267,173 A | 5/1981 | Draper | |
| 4,285,937 A | 8/1981 | Kalvoda | |
| 4,310,466 A | 1/1982 | Edwards | |
| 4,335,121 A | 6/1982 | Phillipps et al. | |
| 4,377,575 A | 3/1983 | Stache et al. | |
| 4,472,393 A | 9/1984 | Shapiro | |
| 4,607,028 A | 8/1986 | Schmidlin | |
| 4,710,495 A | 12/1987 | Bodor | |
| 4,861,765 A | 8/1989 | Mitsukuchi et al. | |
| 4,992,474 A | 2/1991 | Skidmore et al. | |
| 4,994,439 A | 2/1991 | Longenecker et al. | |
| 4,996,335 A | 2/1991 | Bodor | |
| 5,063,222 A | 11/1991 | Komoto et al. | |
| 5,081,113 A | 1/1992 | Claussner et al. | |
| 5,164,194 A | 11/1992 | Hettche | |
| 5,202,316 A | 4/1993 | Claussner et al. | |
| 5,232,919 A | 8/1993 | Scheffler et al. | |
| 5,271,946 A | 12/1993 | Hettche | |
| 5,362,721 A | 11/1994 | Stache et al. | |
| 5,420,120 A | 5/1995 | Boltralik | |
| 5,608,093 A | 3/1997 | Stache et al. | |
| 5,658,549 A | 8/1997 | Akehurst et al. | |
| 5,658,919 A | 8/1997 | Ratnaraj et al. | |
| 5,707,984 A | 1/1998 | Tjoeng et al. | |
| 5,837,699 A | 11/1998 | Sequeira et al. | |
| 5,849,265 A | 12/1998 | Li-Bovet et al. | |
| 5,889,015 A | 3/1999 | Sequeira et al. | |
| 5,914,122 A | 6/1999 | Otterbeck et al. | |

(Continued)

FOREIGN PATENT DOCUMENTS

AU   2003244799 B2   12/2003

(Continued)

OTHER PUBLICATIONS preservative. (n.d.) Dorland's Medical Dictionary for Health Consumers. (2007). Retrieved Nov. 4, 2009 from http://medical-dictionary.thefreedictionary.com/preservative.*
preservative. (n.d.) The American Heritage® Medical Dictionary. (2007). Retrieved Nov. 4, 2009 from http://medical-dictionary.thefreedictionary.com/preservative.*
preservative. (n.d.) Mosby's Medical Dictionary, 8th edition. (2009). Retrieved Nov. 4, 2009 from http://medical-dictionary.thefreedictionary.com/preservative.*
Database Medline Online! US National Library of Medicine (NLM), Bethesda, MD, US: 2000 Portmann D et al: Acceptability of local treatment of allergic rhinitis with a combination of a corticoid (beclomethasone) and an antihistaminic (azelastine); vol. 121, No. 4, 2000, pp. 273-279.

(Continued)

*Primary Examiner* — Johann Richter
*Assistant Examiner* — Thor Nielsen
(74) *Attorney, Agent, or Firm* — Conley Rose, P.C.; Rodney B. Carroll

(57) ABSTRACT

A pharmaceutical product or formulation, which comprises azelastine or a pharmaceutically acceptable salt, solvate or physiologically functional derivative thereof, and a steroid, or a pharmaceutically acceptable salt, solvate or physiologically functional derivative thereof, preferably the product or formulation being in a form suitable for nasal or ocular administration.

48 Claims, No Drawings

U.S. PATENT DOCUMENTS

| Number | Kind | Date | Inventor | Class |
|---|---|---|---|---|
| 5,972,920 | A | 10/1999 | Seidel | |
| 5,981,517 | A | 11/1999 | Bodor | |
| 6,017,963 | A * | 1/2000 | Alfonso et al. | 514/646 |
| 6,057,307 | A | 5/2000 | Sequeira et al. | |
| 6,127,353 | A | 10/2000 | Yuen et al. | |
| 6,136,294 | A | 10/2000 | Adjei et al. | |
| 6,197,761 | B1 | 3/2001 | Biggadike et al. | |
| 6,261,539 | B1 | 7/2001 | Adjei et al. | |
| 6,294,153 | B1 * | 9/2001 | Modi | 424/45 |
| 6,319,513 | B1 | 11/2001 | Dobrozsi | |
| 6,330,938 | B1 | 12/2001 | Herve et al. | |
| 6,391,340 | B1 * | 5/2002 | Malmqvist-Granlund et al. | 424/489 |
| 6,395,300 | B1 | 5/2002 | Straub et al. | |
| 6,416,743 | B1 * | 7/2002 | Fassberg et al. | 424/45 |
| 6,525,228 | B2 | 2/2003 | Chauvin et al. | |
| 6,537,983 | B1 | 3/2003 | Biggadike et al. | |
| 6,583,180 | B2 * | 6/2003 | Link et al. | 514/603 |
| 6,787,532 | B2 | 9/2004 | Biggadike et al. | |
| 6,921,757 | B2 | 7/2005 | Cuenoud et al. | |
| 7,101,866 | B2 | 9/2006 | Biggadike et al. | |
| 7,244,742 | B2 | 7/2007 | Pieper et al. | |
| 7,776,315 | B2 | 8/2010 | Pairet et al. | |
| 2002/0061281 | A1 | 5/2002 | Osbakken et al. | |
| 2002/0076382 | A1 | 6/2002 | Kaplan et al. | |
| 2002/0081266 | A1 | 6/2002 | Woolfe et al. | |
| 2002/0103392 | A1 | 8/2002 | Stache et al. | |
| 2002/0165211 | A1 | 11/2002 | Biggadike et al. | |
| 2002/0173496 | A1 | 11/2002 | Biggadike | |
| 2002/0177581 | A1 | 11/2002 | Biggadike | |
| 2003/0018019 | A1 | 1/2003 | Meade et al. | |
| 2003/0073676 | A1 | 4/2003 | Biggadike et al. | |
| 2003/0109511 | A1 | 6/2003 | Biggadike et al. | |
| 2003/0144257 | A1 | 7/2003 | Biggadike et al. | |
| 2003/0158163 | A1 | 8/2003 | Cuenoud et al. | |
| 2004/0053904 | A1 | 3/2004 | Komoto et al. | |
| 2004/0136918 | A1 | 7/2004 | Garrett et al. | |
| 2004/0204399 | A1 | 10/2004 | Osbakken et al. | |
| 2004/0235807 | A1 | 11/2004 | Weinrich et al. | |
| 2004/0242638 | A1 | 12/2004 | Yanni et al. | |
| 2005/0163724 | A1 | 7/2005 | Miyadai et al. | |
| 2005/0192261 | A1 | 9/2005 | Jost-Price et al. | |
| 2006/0110331 | A1 | 5/2006 | Dang et al. | |
| 2006/0228306 | A1 | 10/2006 | Lane | |
| 2007/0020330 | A1 | 1/2007 | Dang et al. | |
| 2009/0286762 | A1 | 11/2009 | Myles et al. | |
| 2009/0291143 | A1 | 11/2009 | Lulla et al. | |
| 2009/0318397 | A1 | 12/2009 | Lulla et al. | |
| 2010/0152147 | A1 | 6/2010 | Fuge et al. | |

FOREIGN PATENT DOCUMENTS

| Country | Number | | Date |
|---|---|---|---|
| BE | 889563 | A | 11/1981 |
| DE | 1059906 | | 6/1959 |
| DE | 19947234 | | 4/2001 |
| DE | 10152369 | A1 | 5/2002 |
| DE | 3836579 | A1 | 8/2009 |
| EP | 0004773 | | 10/1979 |
| EP | 0057401 | | 8/1982 |
| EP | 0179583 | | 4/1986 |
| EP | 0393658 | | 10/1990 |
| EP | 0416951 | | 3/1991 |
| EP | 0 780 127 | * | 6/1997 |
| EP | 0780127 | * | 6/1997 |
| EP | 1519731 | B1 | 4/2009 |
| EP | 2072051 | A1 | 6/2009 |
| GB | 1191965 | | 5/1970 |
| GB | 1296458 | | 11/1972 |
| GB | 1384372 | | 2/1975 |
| GB | 1438940 | | 6/1976 |
| GB | 1517278 | | 7/1978 |
| GB | 2079755 | | 1/1982 |
| GB | 2088877 | | 6/1982 |
| GB | 2140800 | | 12/1984 |
| GB | 2389530 | A | 12/2003 |
| IL | 109656 | | 2/1998 |
| JP | 04208267 | | 7/1992 |
| JP | 8291072 | | 11/1996 |
| JP | 8291073 | | 11/1996 |
| JP | 2002-053485 | | 2/2002 |
| WO | 8903390 | | 4/1989 |
| WO | 9015816 | | 12/1990 |
| WO | 9104252 | | 4/1991 |
| WO | 9214472 | | 9/1992 |
| WO | 9531964 | | 11/1995 |
| WO | 9619199 | | 6/1996 |
| WO | 9632151 | | 10/1996 |
| WO | 9701337 | | 1/1997 |
| WO | 9705136 | | 2/1997 |
| WO | 9715298 | | 5/1997 |
| WO | 9721721 | | 6/1997 |
| WO | 9721724 | | 6/1997 |
| WO | 9724365 | | 7/1997 |
| WO | 9740836 | | 11/1997 |
| WO | 9746243 | A1 | 12/1997 |
| WO | 9817676 | | 4/1998 |
| WO | 9834596 | | 8/1998 |
| WO | 9848856 | | 11/1998 |
| WO | 9901467 | | 1/1999 |
| WO | 9925359 | | 5/1999 |
| WO | 9932089 | | 7/1999 |
| WO | 0016814 | | 3/2000 |
| WO | 0033892 | | 6/2000 |
| WO | 0038811 | | 7/2000 |
| WO | 0048587 | | 8/2000 |
| WO | 0049993 | | 8/2000 |
| WO | 0066522 | | 11/2000 |
| WO | 0104118 | | 1/2001 |
| WO | 0120331 | | 3/2001 |
| WO | 0154481 | | 8/2001 |
| WO | 0154664 | | 8/2001 |
| WO | 0157025 | | 8/2001 |
| WO | 0162722 | | 8/2001 |
| WO | 0178736 | | 10/2001 |
| WO | 0178739 | | 10/2001 |
| WO | 0178741 | | 10/2001 |
| WO | 0178745 | | 10/2001 |
| WO | 0200199 | | 1/2002 |
| WO | 0200679 | | 1/2002 |
| WO | 0202565 | | 1/2002 |
| WO | 0207767 | | 1/2002 |
| WO | 0208243 | | 1/2002 |
| WO | 0212265 | | 2/2002 |
| WO | 0212266 | | 2/2002 |
| WO | 0213868 | | 2/2002 |
| WO | 0226723 | | 4/2002 |
| WO | 0236106 | | 5/2002 |
| WO | 02051422 | | 7/2002 |
| WO | 02053186 | | 7/2002 |
| WO | 02066422 | | 8/2002 |
| WO | 02070490 | | 9/2002 |
| WO | 02076933 | | 10/2002 |
| WO | 02085296 | | 10/2002 |
| WO | 02088167 | | 11/2002 |
| WO | 02100879 | | 12/2002 |
| WO | 03000241 | | 1/2003 |
| WO | 03013427 | | 2/2003 |
| WO | 03033000 | | 4/2003 |
| WO | 03035668 | | 5/2003 |
| WO | 03040691 | | 5/2003 |
| WO | 03042229 | | 5/2003 |
| WO | 03042230 | | 5/2003 |
| WO | 03048181 | | 6/2003 |
| WO | 03062259 | | 7/2003 |
| WO | 03064445 | | 8/2003 |
| WO | 03066033 | | 8/2003 |
| WO | 03066036 | | 8/2003 |
| WO | 03066656 | | 8/2003 |
| WO | 03072592 | | 9/2003 |
| WO | 03086399 | | 10/2003 |
| WO | 03105856 | A1 | 12/2003 |
| WO | 2004013156 | | 2/2004 |
| WO | 2004019955 | A1 | 3/2004 |
| WO | 2008012338 | A2 | 1/2008 |
| ZA | 872389 | | 4/1987 |

OTHER PUBLICATIONS

Busse W W et al: "Corticosteroid-Sparing Effect of Azelastine in the Management of Bronchial Asthma"—American Journal of Respiratory and Critical Care Medicine, American Lung Association, new York, NW, vol. 153, No. 1, 1996, pp. 122-172, p. 127, col. 1, paragraph 2.

International Search Report under Section 17 UK Patent Office collections, including GB, EP, WO & US patent specifications.

Foreign communication from the priority application—International Search Report, PCT/GB03/02557, Sep. 17, 2003, 3 pages.

Foreign communication from the priority application—International Preliminary Examination Report, PCT/GB03/02557, Aug. 26, 2004, 6 pages.

Foreign communication from a related counterpart application—Examination Report, EP Application 03738280.1, Nov. 10, 2005, 4 pages.

Foreign communication from a related counterpart application—Examination Report, EP Application 03738280.1, Jul. 18, 2007, 5 pages.

Applicants response to foreign communication—EP 03738280.1, May 22, 2006, 36 pages.

Applicants response to foreign communication—EP 03738280.1, Jan. 18, 2008, 17 pages.

May, Percy, et al., "May's Chemistry of Synthetic Drugs," Fifth Edition, 1964, pp. 12-17, Longmans.

ABPI Compendium of Data Sheets and Summaries of Product Characteristics, 1999-2000, Cover page, p. 43 and Index p. 1882, Datapharm Publications Limited, London, Great Britain.

Dykewicz, Mark S., et al., "Diagnosis and Management of Rhinitis: Complete Guidelines of the Joint Task Force on Practice Parameters in Allergy, Asthma and Immunology," Annals of Allergy, Asthma, & Immunology, vol. 81, November (Part II) 1998, pp. 478-518.

Foreign communication from a related counterpart application—Notice of Opposition, EP Application 03738280.1, Feb. 22, 2010, 22 pages.

Office Action dated Sep. 30, 2010, U.S. Appl. No. 12/508,388, filed Jul. 23, 2009, 22 pages.

Office Action dated Sep. 30, 2010, U.S. Appl. No. 12/508,393, filed Jul. 23, 2009, 31 pages.

Patent application entitled "Combination of azelastine and steroids," by Amar Lulla, et al., filed Sep. 10, 2010 as U.S. Appl. No. 12/879,515.

Hodges, Norman, et al., "Antimicrobial Preservative Efficacy Testing," Handbook of Microbiological Quality Control, Pharmaceuticals and Medical Devices, 2000, p. 168 plus cover page and publication page, Rosamund M. Baird, et al., Editor, Taylor & Francis Publisher, USA and Canada.

Herrero, Vanrell, R., "Preservatives in Ophthalmic Formulations: An Overview," Arch. Soc. Esp. Oftalmol, 2007, vol. 82., pp. 531-532.

Johnson, Malcom, "Development of fluticasone propionate and comparison with other inhaled corticosteroids," J. Allergy Clin. Immunol., Apr. 1998, vol. 101, No. 4, Part 2, pp. S434-S439.

Foreign communication from a related counterpart application—CA2,489,427, Examination Report, Jun. 18, 2010, 3 pages.

Foreign communication from a related counterpart application—CA2,489,427, Examination Report, Mar. 24, 2011, 2 pages.

Foreign communication from a related counterpart application—Examination Report, EP Application 03738280.1, Nov. 10, 2005, 4 pages.

Foreign communication from a related counterpart application—Examination Report, EP Application 03738280.1, Jul. 18, 2007, 5 pages.

Foreign communication from a related counterpart application—Notice of Intent to Grant, EP Application 03738280.1, Oct. 23, 2008, 6 pages.

Foreign communication from a related counterpart application—AU2003244799, Examination Report, Nov. 20, 2007, 2 pages.

Foreign communication from a related counterpart application—KR 10-2004-7020819, Examination Report, Aug. 26, 2010, 8 pages.

Gennaro, Alfonso R., ed., et al., Remington: The Science and Practice of Pharmacy, 2000, 20th edition, vol. 1, pp. 785, 830, 831 plus cover page and publication page, Lippincott Williams & Wilkins.

Gilbert, Peter, et al., "Preservation of pharmaceutical products," Encyclopedia of Pharmaceutical Technology, 2002, 2nd edition, vol. 3, p. 2278 plus cover page and publication page, Marcel Dekker, Inc.

Office Action (Final) dated Feb. 18, 2011 (23 pages), U.S. Appl. No. 12/508,388, filed Jul. 23, 2009.

Office Action (Final) dated Feb. 24, 2011 (20 pages), U.S. Appl. No. 12/508,393, filed Jul. 23, 2009.

Reddy, Indra K., ed., Ocular Therapeutics and Drug Delivery: A Multi-Disciplinary Approach, 1996, pp. 382-385 plus cover page and publication page, Technomic Publishing Company, Inc.

Foreign communication from a related counterpart application—Summons to Attend Oral Proceedings, EP Application 03738280.1, Feb. 8, 2011, 1 page.

Foreign communication from a related counterpart application—Examination Report, RU 2005100781, Apr. 23, 2007, 6 pages.

Foreign communication from a related counterpart application—Examination Report, RU 2005100781, May 23, 2008, 3 pages.

Pre-Grant Opposition, Indian Patent Application 2092/KOLNP/2007 dated Jun. 8, 2007, 183 pages.

McNeely, Wendy, et al., "Intranasal Azelastine A Review of its Efficacy in the Management of Allergic Rhinitis," Drugs, 1998, vol. 56, No. 1, pp. 91-114.

ABPI Data Sheet Compendium, 1995-96, cover page plus pp. 38-39, Datapharm Publications Limited, London, Great Britain.

Aurora, Jack, "Nasal Delivery; Development of Nasal Delivery Systems: A Review," Drug Delivery Technology, vol. 2, No. 7, Oct. 2002, 8 pages, http://www.drugdelivelytech.com/ME2/Segments/Publications: Article&id=9EB19EB2F29F462089CE081473F5F3CA.

Block, John H., et al., "Inorganic Medicinal and Pharmaceutical Chemistry," 1986, cover, publication, and preface pages plus p. 100, Indian Edition, Varghese Publishing House, Bombay, India.

Cipla Sixty-Ninth Annual Report 2004-2005, cover pages, information page, plus pp. 3, 5, and 44.

Drouin, Michel A., et al., "Adding Loratadine to Topical Nasal Steroid Therapy Improves Moderately Severe Seasonal Allergic Rhinoconjunctivitis," Advances in Therapy, vol. 12, No. 6, Nov./Dec. 1995, pp. 340-349, Health Communications Inc.

Foreign communication from a related counterpart application—Translation of Office Action, Israel Patent Application 165771, Jul. 11, 2011, 3 pages.

Hodges, N. A., et al., "Preservative Efficacy Tests in Formulated Nasal Products: Reproducibility and Factors Affecting Preservative Activity," J. Pharm. Pharmacol., 1996, vol. 48, pp. 1237-1242.

Applicants response to foreign communication—KR10-2004-7020819, Dec. 27, 2010, 18 pages.

Prescribing Information for Asteproe®, Nov. 2010, 20 pages, Meda Pharmaceuticals Inc., Somerset, NJ, US.

Prescribing Information for Rhinocort Aqua™, Dec. 2010, 32 pages, AstraZeneca LP, Wilmington, DE, US.

Product Information, Nasonex®, Aug. 2001, 22 pages, Schering Corporation, Kenilworth, NJ, US.

Safety Data Sheet, SDS No. 110556, Jul. 4, 2008, V14, Flonase Nasal Spray, 5 pages, GlaxoSmithKline.

Safety Data Sheet, SDS No. 110536, Jun. 23, 2008, V13, Beconase Hayfever Allergy Spray, 5 pages, GlaxoSmithKline.

Wiseman, Lynda R., et al., "Intranasal Fluticasone Propionate: A Reappraisal of its Pharmacology and Clinical Efficacy in the Treatment of Rhinitis," Drugs, 1997, vol. 53, No. 5, pp. 885-907, Adis International Limited.

World Review 2001: The Pharmaceutical Market, vol. 1 International, Ims Health, 2001, cover, preface, and copyright pages plus pp. 4-42 and 5-1 through 5-11, IMS A.G.

Opposition to EP 1518731, Aug. 8, 2011, 19 pages.

Berge, Stephen M., et al., "Pharmaceutical Salts," Journal of Pharmaceutical Sciences, vol. 66, No. 1, Jan. 1977, pp. 1-19.

Avicel® RC/CL, Microcrystalline Cellulose and Carboxymethylcellulose Sodium, NF Dispersible Cellulose, BP, Specifications and Analytical Methods, RC-16 Updated Oct. 1995 (Feb. 1999), 6 pages, FMC BioPolymer.

Baena-Cagnani, Carlos E., "Safety and Tolerability of Treatments for Allergic Rhinitis in Children," Drug Safety 2004, vol. 27, No. 12, pp. 883-898, ADIS Data Information BV.

Galant, Stanley P., et al., "Clinical Prescribing of Allergic Rhinitis Medication in the Preschool and Young School-Age Child, What are the Options?," BioDrugs2001, vol. 15, No. 7, pp. 453-463, ADIS International Ltd.

Wang, De-Yun, "Treatment of Allergic Rhinitis: H1-Antihistamines and Intranasal Steroids," Current Drug Targets—Inflammation & Allergy, 2002, vol. I, pp. 215-220, Bentham Science Publishers Ltd.

Meltzer, Eli O., "Allergic rhinitis: Managing the pediatric spectrum," Allergy and Asthma Proceedings, Jan.-Feb. 2006, vol. 27, No. 1, pp. 2-8, Oceanside Publications, Inc., USA.

Ratner, Paul H., et al., "Combination therapy with azelastine hydrochloride nasal spray and fluticasone propionate nasal spray in the treatment of patients with seasonal allergic rhinitis," Annals of Allergy, Asthma & Immunology, Jan. 2008, vol. 100, Cover page, publishing page, pp. 74-81.

Ratner, Paul H., et al., "A Comparison of the Efficacy of Fluticasone Propionate Aqueous Nasal Spray and Loratadine, Alone and in Combination, for the Treatment of Seasonal Allergic Rhinitis," The Journal of Family Practice, Aug. 1998, vol. 47, No. 2, pp. 118-125, Appleton & Lange.

Nielsen, Lars P., "Comparison of Intranasal Corticosteroids and Antihistamines in Allergic Rhinitis, A Review of Randomized, Controlled Trials," Am. J. Respir Med. 2003, vol. 2, No. 1, Cover page, publishing page, pp. 55-65., ADIS International Limited.

Nielsen, Lars Peter, et al., "Intranasal Corticosteroids for Allergic Rhinitis, Superior Relief?," Drugs 2001, vol. 61, No. 11, pp. 1563-1579, ADIS International Ltd.

Di Lorenzo, G., et al., "Randomized Placebo-controlled Trial Comparing fluticasone aqueous nasal spray in mono-therapy, fluticasone plus cetirizine, fluticasone plus montelukast and cetirizine plus montelukast for seasonal allergic rhinitis," Clin. Exp. Allergy, 2004, vol. 34, pp. 259-267, Blackwell Publishing Ltd.

Akerlund, Anders, et al., "Clinical trial design, nasal allergen challenge models, and considerations of relevance to pediatrics, nasal polyposis, and different classes of medication," J. Allergy Clin. Immunol., Mar. 2005, vol. 115, No. 3, pp. S460-S482.

Howarth, P. H., "A comparison of the anti-inflammatory properties of intranasal corticosteroids and antihistamines in allergic rhinitis," Allergy 2000, vol. 62, pp. 6-11, Munksgaard 2000.

Salib Rami Jean, et al., "Safety and Tolerability Profiles of Intranasal Antihistamines and Intranasal Corticosteroids in the Treatment of Allergic Rhinitis," Drug Safety 2003, vol. 26, No. 12, Cover page, publication page, pp. 863-893, ADIS Data Information BV.

Simpson, Richard J., "Budesonide and terfenadine, separately and in combination, in the treatment of hay fever," Annals of Allergy, Dec. 1994, vol. 73, Cover page, publication page, pp. 497-502.

Juniper, E F., et al., "Comparison of beclomethasone dipropionate aqueous nasal spray, astemizone, and the combination in the prophylactic treatment of ragweed pollen-induced rhinoconjunctivitis," Journal of Allergy and Clinical Immunology, Mar. 1989, vol. 83, No. 3, Cover page, Publications page, pp. 627-633, American Academy of Allergy and Immunology, C.V. Mosby Co.

Barnes, M. L., et al., "Effects of levocetirizine as add-on therapy to fluticasone in seasonal allergic rhinitis," Clinical and Experimental Allergy, Jan. 27, 2006, vol. 36, pp. 676-684, Blackwell Publishing Ltd.

Applicants response to foreign communication—EP 03738280.1 (EP Patent 1519731), Sep. 6, 2010, 15 pages.

File history of Australian Patent Application No. AU2003244799, 38 pages.

File history of Korean Patent Application No. 10-2004-7020819, 89 pages.

File history of Mexican Patent Application No. PA/a/2004/01266 (now Patent No. 265349), 86 pages.

File history of South African Patent Application No. 2005/0331 (now Patent No. 2005/0331), 18 pages.

Applicants response to foreign communication—CA 2489427, Dec. 20, 2010, 10 pages.

Applicant Response to foreign communication EP Patent 1519731, Aug. 11, 2011, 252 pages.

Maus Exhibit B, Aug. 2011.

Nielsen, et al., "Intranasal corticosteroids for allergic rhinitis: superior relief?" Drugs, 2001, vol. 61, No. 11, pp. 1535-1691.

Opponent's R116 Submission for EP1519731, 2011.

CIPLA's response to Statement of Opposition for EP1519731, 2011.

Shenfield, "Fixed drug combinations: which ones can be recommended?" Current Therapeutics, 1986, pp. 15-29.

Opponent's Statement of Opposition for EP1519731, 2011.

Result of oral proceedings dated Oct. 12, 2011 of EP Patent No. 1519731.

Opponent's submission dated Oct. 6, 2011 to EP Patent No. 1519731.

Patentee's submission dated Oct. 5, 2011 to EP Patent No. 1519731.

Patentee's submission dated Sep. 29, 2011 regarding list of attendees at oral proceedings on EP Patent No. 1519731.

Opponent's submission dated Sep. 23, 2011 regarding list of attendees at oral proceedings on EP Patent No. 1519731.

Opponent's submission dated Sep. 23, 2011 regarding additional documents on EP Patent No. 1519731.

Patentee's submission dated Sep. 19, 2011 on EP Patent No. 1519731.

Patentee's response of Sep. 6, 2010 of EP Patent No. 1519731.

Hampel, Frank C., et al., Double-blind, placebo-controlled study of azelastine and fluticasone in a single nasal spray delivery device, Annals of Allergy, Asthma & Immunology, Aug. 2010, vol. 105, pp. 168-173.

Biggadike, Keith, Letter to the Editor, "Fluticasone furoate/fluticasone propionate—different drugs with different properties," The Clinical Respiratory Journal, 2011, pp. 183-184.

Rapid response report: summary with critical appraisal, fluticasone furoate versus fluticasone propionate for seasonal allergic rhinitis: a review of the clinical and cost-effectiveness, Jun. 13, 2011, Fluticasone Furoate for Seasonal Allergic Rhinitis.

Office Action dated Sep. 9, 2011 of U.S. Appl. No. 12/508,388 filed Jul. 23, 2009.

Office Action dated Sep. 15, 2011 of U.S. Appl. No. 12/508,393 filed Jul. 23, 2009.

Search Report dated May 12, 2009 of EP 09075101.

Search Report dated May 12, 2009 of EP 09075100.

Mealy, N. E., et al., "Ciclesonide: treatment of allergic rhinitis antiallergy/antiasthmatic," Drugs of the Future, Prous Science, ES, vol. 26, No. 11, Nov. 2001, pp. 1033-1039.

Office Action dated Jul. 11, 2011—20632 IL.

Office Action dated Aug. 31, 2010 (6 pages), U.S. Appl. No. 12/374,523 filed on Jan. 21, 2009.

Applicants' response dated Oct. 6, 2010 (8 pages) in U.S. Appl. No. 12/374,523 filed on Jan. 21, 2009.

Office Action dated Nov. 30, 2010 (16 pages), U.S. Appl. No. 12/374,523 filed on Jan. 21, 2009.

Applicants' response dated Feb. 24, (2010) 2011 (8 pages) in U.S. Appl. No. 12/374,523 filed on Jan. 21, 2009.

Office Action (Final) dated May 3, 2011 (8 pages), U.S. Appl. No. 12/374,523 filed on Jan. 21, 2009.

Applicants' response dated Jun. 22, 2011 (9 pages) in U.S. Appl. No. 12/374,523 filed on Jan. 21, 2009.

Notice of Non-responsive Amendment dated Jul. 6, 2011 (3 pages), U.S. Appl. No. 12/374,523 filed on Jan. 21, 2009.

Applicants' response dated Sep. 6, 2011 (8 pages) in U.S. Appl. No. 12/374,523 filed on Jan. 21, 2009.

Spector, Sheldon, "Ideal pharmacotherapy for allergic rhinitis," J Allergy Clin Immunol, vol. 103, No. 3, Part 2, pp. S386-S387, 1999.

Duonase Data Sheet, "The complete rhinitis control," 6 pages, Cipla Limited, Mumbai, India, 2004.

Product Specification Bulletin, Avicel® RC-591, Bulletin AVC591-SPEC-02/09.RS, 2 pages, FMC BioPolymer, Feb. 2009.

Product Specification Bulletin, Avicel® CL-611, Bulletin AVC611-SPEC-02/09.RS, 2 pages, FMC BioPolymer, Feb. 2009.

File history of Brazilian Patent Application No. PI 0312128-3, 27 pages, Apr. 2011.

File history of Canadian Patent Application No. 2,489,427, 19 pages, Dec. 2010.

File history of Polish Patent Application No. P-373001, 95 pages, May 2011.

File history of Russian Patent Application No. RU 2361593 C2, 65 pages, Apr. 2009.

Salib, et al.; "Safety and Tolerability Profiles of Intranasal Anihistaminese and Intranasal Corticosteroids in the Treatment of Allergic Rhinitis;" Drug Safety; 2003; vol. 26, No. 12, pp. 829-911.
Office Action dated Apr. 7, 2011 (3 pages) from counterpart application, AU2009243420.
Moreno-Vargas, et al., "Synthesis and gylcosidase inhibitory activities of 5-(1',4'-dideoxy-1',4'-imino-D-erythrosyl)-2-methyl-3-furoic acid (=5-[(3S,4R)-3,4-dihydroxypyrrolidin-2-yl]-2methylfuran-3-carboxylic acid) derivatives: new leads as selective alpha-L-fucosidase and beta-galactosidase inhibitors," Helvetica Chimica Acta, vol. 86, pp. 1894-1913, 2003.
Nathan, et al., "A once daily fluticasone proprionate aqueous nasal spray is an effective treatment for seasonal allergic rhinitis," Annals of Allergy, 1991, vol. 67, pp. 332-338.
Nelson, Harold, S., et al., Fluticasone propionate-salmeterol combination provides more effective asthma control than low-dose inhaled corticosteroid plus montelukast, J. Allergy Clin. Immunol., vol. 106, No. 6, Dec. 2000, pp. 1088-1095.
Ong, John T. H., et al., "Micellar solubilization of timobesone acetate in aqueous and aqueous propylene glycol solutions of nonionic surfactants," Pharmaceutical Research, vol. 5, No. 11, 1988, pp. 704-708.
Ong, John T. H., et al., "Intrinsic potencies of novel thiol ester corticosteroids RS-85095 and RS-21314 as compared with clobetasol 17-propionate and fluocinonide," Arch Dermatol, vol. 125, Dec. 1989, pp. 1662-1665.
Onrust, et al., "Mometasone furoate, a review of its intranasal use in allergic rhinitis," Drugs, vol. 56, No. 4, Oct. 1998, pp. 725-745, vol. 21.
Phillips, G. H., et al., "Synthesis and structure activity relationships in a series of anti-inflammatory corticosteroid analogues, halomethyl androstane—17B-carbothioates and—17B-carboselenoates," Journal of Medicinal Chemistry, 1994, vol. 37, pp. 3717-3729.
Product Information Flonase (Fluticasone proprionate) Nasal Spray 50 mcg, 2004, pp. 1-13.
Product Information Rhinocort Aqua (budesonide) Nasal Spray 32 mcg, 2005, pp. 1-2.
Sakagami, et al., "Mucoadhexive BDP microspheres for powder inhalation—their unique pharmacokinetic-pharmacodynamic profiles," Respiratory Drug Delivery, vol. VI, pp. 193-199, 1998.
Sandham, et al., "Synthesis and biological properties of novel glucocorticoid androstene C-17 furoate esters," Bioorganic & Medicinal Chemistry, 2004, vol. 12, pp. 5213-5224.
Scadding, et al., "Clinical and physiological effects of fluticasone propionate aqueous nasal spray in the treatment of perennial rhinitis," Rhinology, 1991, Suppl. 11, pp. 37-43.
Settipane, et al., "Triamcinolone acetonide aqueous nasal spray in patients with seasonal ragweed allergic rhinitis: a placebo-controlled, double-blind study," Clin. Ther., 1995, vol. 17, No. 2, pp. 252-263.
Shapiro, et al., "17-esters and 17,21-diesters of 9-alpha, 11-beta-dichlorocorticoids. Synthesis and anti-inflammatory activity," Steroids, vol. 9, No. 2, pp. 143-156, 1967.
Shapiro, et al., "Synthesis and structure-activity studies of corticosteroid 17-heterocyclic aromatic esters. 1. 9-alpha, 11-beta dichloro series," Journal of Medicinal Chemistry, vol. 30, No. 6, pp. 1068-1073, 1987.
Shapiro, et al., "17 heteroaroyl esters of corticosteroids 2. 11 beta hydroxy series," Journal of Medicinal Chemistry, American Chemical Society, Washington, US, vol. 30, No. 9, 1987, pp. 1581-1588.
Smith, et al., "In vitro glucocorticoid receptor binding and transcriptional activation by topically active glucocorticoids," Arzneimettelforschung, 1998, 48(II)(9), pp. 956-959.
Smith, N., et al., "Comparison of the electroosmotic flow profiles and selectivity of stationary phases used in capillary electrochromatography," Journal of Chromatography A., vol. 832, 1999, pp. 41-54.
Souness, et al., "Immunosuppressive and anti-inflammatory effects of cyclic AMP phosphodiesterase (PDE) type 4 inhibitors," Immunopharmacology, 2000, vol. 47, Nos. 2/3, pp. 127-162.
Stempel, et al., "Treatment of allergic rhinitis: an evidence-based evaluation of nasal corticosteroids versus nonsedating antihistamines," Am. J. Man. Care, 1998, vol. 4, pp. 89-96.

Study No. 03DMW062—"Pharmacokinetics of GW685698X and CC118781 (fluticasone propionate) when co-administered by the intratracheal or intravenous route to the anaesthetised white pig," 2004.
Study No. B30947—"The Pharmacokinetics of GW685698X and CC118781 following intratracheal co-administration to the anaesthetised white pig," 2003.
Szefler, Stanley J., et al., Chapter 21, "Glucocorticoids in severe asthma: mechanisms of action and route of administration," Difficult Asthma, pp. 371-375, Martin Dunitz Ltd., Informa Health Care, 1999.
Togashi, et al., 9-fluoro-11B, 17, 21-trihyrdroxy-16a-methyl-1,4-pregnadiene-3, 20-dione 21- cyclohexanecarboxylate 17-cyclopropanecarboxylate (ST126); Oyo Yakuri, 2002, vol. 63, No. 5/6, pp. 61-77.
Undem, et al., "Neural integration and allergic disease," J. Allergy Clin. Immunol., 2000, vol. 106, No. 5, pp. S213-S220.
The United States Pharmacopoeia, 23rd Ed., US Pharmacopoeia Convention, Inc., Rockville MD, 1995, pp. 1843-1844, "Physical Tests/(941) X-Ray Diffraction."
Van As, et al., "Once daily flluticasone propionate is as effective for perennial allergic rhinitis as twice daily beclomethasone dipropionate," J. Allergy Clin. Immunol., 1993, vol. 91, No. 6, pp. 1146-1154.
Van Bavel, et al., "Ocular efficacy and clinician overall evaluation of intranasal fluticasone proprionate (FP) versus loratadine (LOR) in seasonal allergic rhinitis (SAR)," Annals of Allergy, Asthma, & Immunology, 1997, vol. 78, p. 128, Abstract P101.
Wenkert, et al., "Short syntheses of furan and catechol derivatives. A synthesis of hydrourushiol1,2," Journal American Chemical Society, vol. 105, pp. 2021-2029, 1983.
Westlund, et al., "Fluticasone propionate aqueous nasal spray 200 mg once daily provides relief of ocular symptoms associated with seasonal allergic rhinitis," 57th Annual Meeting of the American Academy of Allergy, Asthma and Immunology, New Orleans LA, Mar. 16-21, 2001, Abstract No. 522.
Woodford, et al., "Activity and bioavailability of a new steroid (Timobesone acetate) in cream and ointment compared with Lidex and Dermovate creams and ointments and Betnovate cream," Int'l Journal of Pharmaceutics, 1985, vol. 26, pp. 145-155.
Observations on patentability of the object of the patent application PV 2003-352 (Czech Republic), 2003.
Notice of Opposition to the grant of patent on Patent Application No. 762/2001 (140397) (Pakistan), 2010.
CIPLA Annual Report Extract; 2010; (report shows that they launched an FF+azelastine product in 2010).
Declaration of Geena Malhotra for EP1519731 dated Aug. 11, 2011.
Declaration of Joachim Maus for EP1519731 dated Aug. 10, 2011.
Vanrell, "Preservatives in ophthalmic formulations: an overview," Arch. Soc. Esp. Oftalmol., 2007, vol. 82, pp. 531-532.
Malhotra Exhibit A, Aug. 2011.
"Azelastine," STN Registry No. 58581-89-8, STN Registry File, Retrieved Nov. 23, 2010, p. 1.
"Fluticasone Furoate," STN Registry No. 397864-44-7, STN Registry File, Retrieved Nov. 23, 2010, p. 1.
Astepro (azelastine HCI) Nasal Spray 0.15%, Meda Pharmaceuticals Inc., 2009, Press Release, pp. 1-4.
Aigbirhio, Franklin I., et al., "Automated radiosynthesis of no-carrier-added [S-fluoromethyl-18F]Fluticasone propionate as a radiotracer for lung deposition studies with PET," Journal of Labelled Compounds and Radiopharmaceuticals, vol. 39, No. 7, 1997, pp. 569-584.
Austin, et al., "Mometasone furoate is a less specific glucocorticoid than fluticasone propionate," Eur. Respir. J., 2002, vol. 20, pp. 1386-1392.
Banov, et al., "Once daily intranasal fluticasone propionate is effective for perennial allergic rhinitis," Annals of Allergy, 1994, vol. 73, pp. 240-246.
Baumgarten, C., et al., "Initial treatment of symptomatic mild to moderate bronchial asthma with the salmeterol/fluticasone propionate (50/250μg) combination product (SAS 40023)," European Journal of Medical Research, 2002, vol. 7, pp. 1-7.

Berstein, et al., "Treatment with intranasal fluticasone propionate significantly improves ocular symptons in patients with seasonal allergic rhinitis," Clin. Exp. Allergy, 2004, vol. 34, pp. 952-957.

Brooks, et al', "Spectrum of seasonal allergic rhinitis symptom relief with topical corticoid and oral antihistamine given singly or in combination," American Journal of Rhinology, 1996, vol. 10, No. 3, pp. 193-199.

Bryson, et al., "Intranasal fluticasone propionate: a review of its pharmacodynamic and pharmacokinetic properties, and therapeutic potential in allergic rhinitis," Drugs, 1992, vol. 43, No. 5, pp. 760-775.

Busse, William, et al., "Steroid-sparing effects of fluticasone propionate 100µg and salmeterol 50 µg. administered twice daily in a single product in patients previously controlled with fluticasone propionate 250 µg administered twice daily," J. Allergy Clin. Immunol., vol. 111, No. 1, Jan. 2003, pp. 57-65.

CAS Registry No. 102113-40-6, 2004.

CAS Registry No. 90566-53-3, "Fluticasone," Nov. 16, 1984.

Chapman, et al., "Anti-inflammatory activity of inhaled mometasone furoate in allergic mice," Arzneimettelforschung ("Drug Research"), 1998, vol. 48, No. 4, pp. 384-391.

Daley-Yates, et al., "Systemic bioavailability of fluticasone propionate administered as nasal drops and aqueous nasal spray formulations," Br. J. Clin. Pharmocol., 2001, vol. 51, pp. 103-105.

Derby, et al., "Risk of cataract among users of intranasal corticosteroids," J. Allergy Clin. Immunol., 2000, vol. 105, No. 5, pp. 912-916.

Dewester, et al., "The efficacy of intranasal fluticasone propionate in relief of ocular symptoms associated with seasonal rhinitis," Allergy and Asthma Proc., 2003, vol. 24, No. 5, pp. 331-337.

Dictionary of Organic Compounds, 6th Ed., vol. 1, p. 3234, definition of "fluticasone," Chapman & Hall, 1996.

Dolovich, et al., "Multicenter trial of fluticasone propionate aqueous nasal spray in ragweed allergic rhinitis," Annals of Allergy, 1994, vol. 73, No. 2, pp. 147-153.

Fowler, Stephen J., et al., "Step-down therapy with low-dose fluticasone-salmeterol combination or medium-dose hydrofluoroalkane 134a-beclomethasone alone," J. Allergy Clin. Immunol., vol. 109, No. 6, Jun. 2002, pp. 929-935.

Garner, R. C., et al., "A validation study comparing accelerator MS and liquid scintillation counting for analysis of 14C-labelled drugs in plasma, urine and faecal extracts," Journal of Pharmaceutical and Biomedical Analysis, vol. 24, 2000, pp. 197-209.

Gawchik, et al., "Comparison of intranasal triamcinolone acetonide with oral loratadine in the treatment of seasonal ragweed-induced allergic rhinitis," Am. J. Man. Care, 1997, vol. 3, No. 7, pp. 1052-1058.

Harding, "The human pharmacology of fluticasone propionate," Respiratory Medicine, 1990, vol. 84, Suppl. A, pp. 25-29.

Howland, "Fluticasone propionate: topical or systemic effects?" Clinical and Experimental Allergy, 1996, vol. 26, Suppl. 3, pp. 18-22.

Isogai, et al., "Binding affinities of mometasone furoate and related compounds including its metabolites for the glucocorticoid receptor of rat skin tissue," J. Steroid Biochem. Mol. Biol., 1993, vol. 44, pp. 141-145.

Johansson, Gunnar, et al., "Comparison of salmeterol/fluticasone propionate combination with budesonide in patients with mild-to-moderate asthma," Clin. Drug Invest., vol. 21, No. 9, 2001, pp. 633-642, 11 pages.

Juniper, Elizabeth F., et al., "Impact of inhaled salmeterol/fluticasone propionate combination product versus budesonide on the health-related quality of life of patients with asthma," Am. J. Respir. Med., vol. 1, No. 6, 2002, pp. 435-440.

Kenley, Richard A., et al., "An automated, column-switching HPLC method for analyzing active and excipient materials in both cream and ointment formulations," Drug Development and Industrial Pharmacy, vol. 11 (9 & 10), 1985, pp. 1781-1796.

Kertesz, Denis J., et al., "Thiol esters from steroid 17β-carboxylic acids: carboxylate activation and internal participation by 17 α-acylates," J. Org. Chem., vol. 51, 1986, 14 pages.

Kooreman, et al., "The synthesis of 17-esters of corticosteroids protection of 11β-hydroxyl of the trimethylsilyl group," Synthetic Communications, vol. 1, No. 2, pp. 81-87, 1971.

Laforce, et al., "Fluticasone propionate: an effective alternative treatment for seasonal allergic rhinitis in adults and adolescents," J. Fam. Pract., 1994, vol. 38, No. 2, pp. 145-152.

Lane, S. J., et al., "Evaluation of a new capillary electrochromatography/mass spectrometry interface using short columns and high field strengths for rapid and efficient analyses," Rapid Communications in Mass Spectrometry, vol. 10, 1996, pp. 733-736.

Lewis, Sarah A., et al., "Association of specific allergen sensitization with socioeconomic factors and allergic disease in a population of Boston women," J. Allergy Clin. Immunol., vol. 107, No. 4, Apr. 2001, pp. 615-622.

Li, et al., "Synthesis of aryl 5-(2-chlorophenyl)-2-furoates under phase transfer catalysis," Synthetic Communications, vol. 32, No. 20, pp. 3081-3086, 2002.

Linder, "Symptom scores as measurements of the severity of rhinitis," Clinical Allergy, 1988, vol. 18, pp. 29-37.

Lutsky, et al., "A novel class of potent topical antiinflammatory agents: 17-benzolyated, 7a-halogeno substituted corticosteroids," Arzneimettelforschung ("Drug Research"), 1978, vol. 29, No. 11, pp. 1662-1667.

Lyseng-Williamson, Katherine A., et al., "Inhaled salmeterol/fluticasone propionate combination in chronic obstructive pulmonary disease," Am. J. Respir. Med., vol. 1, No. 4, 2002, pp. 273-282.

Mahoney, Janette M., et al., "Drug effects on the neovascularization response to silver nitrate cauterization of the rat cornea," Current Eye Research, vol. 4, No. 5, 1985, pp. 531-535.

Millard, Jeffrey W., et al., "Solubilization by cosolvents establishing useful constants for the log-linear model," Int'l Journal of Pharmeceutics, vol. 245, 2002, pp. 153-166.

Mistry, Nisha, et al., "Characterisation of impurities in bulk drug batches of fluticasone propionate using directly coupled HPLC-NMR spectroscopy and HPLC-MS," Journal of Pharmaceutical and Biomedical Analysis, vol. 16, 1997, pp. 697-705.

Mistry, Nisha, et al., "Impurity profiling in bulk pharmaceutical batches using 19F NMR spectroscopy and distinction between monomeric and dimeric impurities by NMR-based diffusion measurements," Journal of Pharmaceutical and Biomedical Analysis, vol. 19, 1999, pp. 511-517.

Office Action dated Mar. 29, 2011 (3 pages) from counterpart application, AU2009243422.

Astelin (azelastine hydrochloride) Nasal Spray, MedPointe Pharmaceuticals, 2006, U.S. Physicians Desk Reference, pp. 1876-1877.

Veramyst (fluticasone furoate) Nasal Spray, GlaxoSmithKline, 2007, Summary Sheet, pp. 1-20.

Barnes, Peter J., "Chronic obstructive pulmonary disease: new opportunities for drug development," Trends in Pharmacological Sciences, vol. 19, No. 10, 1998, pp. 415-423.

Barnes, Peter J., "Novel approaches and targets for treatment of chronic obstructive pulmonary disease," American Journal of Respiratory and Critical Care Medicine, vol. 160, 1999, pp. S72-S79.

Barnes, Peter J., "Efficacy of inhaled corticosteroids in asthma," The Journal of Allergy and Clinical Immunology, vol. 102, No. 4, 1998, pp. 531-538, 1998.

Bowler, Simon, "Long acting beta agonists," Australian Family Physician, vol. 27, No. 12, 1998, pp. 1115, 1117-1118, plus cover.

Knobil, K., et al., "Adding salmeterol is more effective than increasing the dose of fluticasone for patients with asthma who are symptomatic on low dose fluticasone," European Respiratory Review, Copenhagen, DK, vol. 12, Suppl. 29, Dec. 1998 (1998-12), pp. 19S-20S.

Lumry, William R., "A review of the preclinical and clinical data of newer intranasal steroids in the treatment of allergic rhinitis," Allergy Clin. Immunol., Oct. 1999, 104 (4 Pt 1), pp. S150-S158 plus one correction page.

Meltzer, et al., "Onset of therapeutic effect of fluticasone propionate aqueous nasal spray," Ann. Allergy Asthma Immunol., 2001, vol. 86, No. 3, pp. 286-291.

Möllmann, H., et al., Handbook of pharmacokinetic/pharmacodynamic correlation, Chapter 14, Pharmacokinetic-Pharmacodynamic Correlations of Corticosteroids, 323-336, CRC Press, 1995.

Naedele-Risha, R., et al., "Dual components of optimal asthma therapy: scientific and clinical rationale for the use of long acting beta-agonists with inhaled corticosteroids," The Journal of the American Osteopathic Association, vol. 101, No. 9, Sep. 2001, pp. 526-533.

O'Conner, B. J., "Combination therapy," Pulmonary Pharmacology and Therapeutics, vol. 11, No. 5/6, 1998, pp. 397-399.

Holgate, Stephen T., Difficult Asthma, 1999, cover page and publishing information.

PCT/GB01/03495, International Preliminary Examination Report, date of mailing: Aug. 30, 2002.

Popper, T. L., et al., "Structure-activity relationship of a series of novel topical corticosteroids," Journal of Steroid Biochemistry, 1987, vol. 27, pp. 837-843.

Tanaka, et al., "Synthesis of 4H-furo[3,2-b]indole derivatives. III (1). Preparation of 4H-furo[3,2-b]indole-2-carboxylic acid derivatives," Journal Heterocyclic Chemistry, vol. 16, pp. 785-788, 1979.

Ueno, et al., "Synthesis and evaluation of antiinflammatory activities of a series of corticosteroid 17. Alpha-esters containing a functional group," Journal of Medicinal Chemistry, American Chemica Society, vol. 34, No. 8, Aug. 1991, pp. 2468-2473.

Van Der Molen, et al., "Effects of the long acting beta agonist formoterol on asthma control in asthmatic patients using inhaled corticosteroids," Thorax, vol. 52, No. 6, 1997, pp. 535-539.

Comparative data of azelastine with steroids, 2011.

Malhotra Exhibit B, Aug. 2011.

Pettersson, Bertil, et al., "Re-evaluation of the classical mycoplasma lipophilum cluster (Weisburg, et al., 1989) and description of two new clusters in the hominis group based on 16S rDNA sequences," Int'l Journal of Systematic & Evolutionary Microbiology, 2001, vol. 51, pp. 633-643.

* cited by examiner

COMBINATION OF AZELASTINE AND STEROIDS

This application is a §371 National Stage Application of International Application No. PCT/GB03/02557, filed on 13 Jun. 2003, claiming the priority of Great Britain Patent Application No. 0213739.6 filed on 14 Jun. 2002, the entire disclosures of which are herein incorporated by reference in their entirety.

The present invention relates to pharmaceutical products and formulations. More particularly the present invention relates to pharmaceutical products and formulations useful for preventing or minimising allergic reactions. More particularly, but not exclusively, the present invention relates to pharmaceutical products and formulations for nasal and ocular use.

Such allergic reactions commonly comprise the allergy-related and vasomotor-related symptoms and the rhinovirus-related symptoms.

It is known to use antihistamines in nasal sprays and eye drops to treat allergy-related conditions. Thus, for example, it is known to use the antihistamine azelastine (usually as the hydrochloride salt) as a nasal spray against seasonal or perennial allergic rhinitis, or as eye drops against seasonal and perennial allergic conjunctivitis.

It is also known to treat these conditions using a corticosteroid, which will suppress nasal and ocular inflammatory conditions. Among the corticosteroids known for nasal use are, for example, beclomethasone, mometasone, fluticasone, budesonide and cyclosenide. Corticosteroids known for ocular anti-inflammatory use include betamethasone sodium, dexamethasone sodium and prednisolone acetate, for example.

It would be highly desirable, however, to provide a treatment that combines the effects of anti-histamine treatments and steroid treatments, in a pharmaceutically acceptable formulation, which is tolerated in situ, without significantly disrupting the potency of the constituent pharmaceuticals.

We have now found that, very surprisingly, azelastine (4-[(4-Chlorophenyl)methyl]-2-(hexahydro-1-methyl-1H-azepin-4-yl)-1(2H)-phthalazinone), or a pharmaceutically acceptable salt, solvate or physiologically functional derivative thereof, preferably in salt form and even more preferably in the form of the hydrochloride salt, can advantageously be combined with a steroid, or a pharmaceutically acceptable salt, solvate or physiologically functional derivative thereof, to provide a stable, very effective combination product or formulation preferably for nasal or ocular treatment. The combination can provide, in a single administration or dosing regime, the antihistaminic properties of azelastine and the anti-inflammatory (and/or other) properties of the steroid, without any significant interference between the two, or adverse reaction in situ.

In one aspect the invention provides a pharmaceutical formulation comprising azelastine or a pharmaceutically acceptable salt, solvate or physiologically functional derivative thereof and a steroid, preferably a corticosteroid, or a pharmaceutically acceptable salt, solvate or physiologically functional derivative thereof the formulation preferably being in a form suitable for administration nasally or ocularly. In an embodiment, the formulation contains the steroid in an amount from about 50 micrograms/ml to about 5 mg/ml of the formulation. In an embodiment, the formulation contains a suspension containing 0.0005% to 2% (weight/weight of the formulation) of azelastine or a pharmaceutically acceptable salt of azelastine, and from 0.0357% (weight/weight of the formulation), alternatively from 0.5%, to 1.5% (weight/weight of the formulation) of said steroid. In an embodiment, the formulation contains a suspension containing from 0.001% to 1% (weight/weight of the formulation) azelastine, or salt thereof, and from 0.0357% (weight/weight of the formulation), alternatively from 0.5%, to 1.5% (weight/weight of the formulation) steroid.

The term "physiologically functional derivative" as used herein denotes a chemical derivative of any of the specific therapeutic agents described herein having the same or similar physiological function as the free base therapeutic agent and, for example, being convertible in the body thereto. According to the present invention, examples of physiologically functional derivatives include esters.

The preferred forms of formulations of the invention are nasal drops, eye drops, nasal sprays, nasal inhalation solutions or aerosols or insufflation powders.

Preferred embodiments of the invention can comprise stable aqueous solutions of azelastine or one or more of its salts, in combination with steroids which may be beclomethasone, mometasone, fluticasone, budesonide or cyclosenide, which can be used in the form of inhalation solution, pressurized aerosol, eye drops or nasal drops, and in a particular preferred embodiment, in the form of a spray (preferably a nasal spray). The spray can, for example, be formed by the use of a conventional spray-squeeze bottle or a pump vaporizer. In addition, it is also possible to use compressed gas aerosols. In a preferred embodiment, 0.03 to 3 mg of azelastine base and 0.05 to 0.15 mg of the steroid should be released per individual actuation.

The formulations preferably contain a preservative and/or stabilizer. These include, for example: ethylene diamine tetra-acetic acid (edetic acid) and its alkali salts (for example dialkali salts such as disodium salt, calcium salt, calcium-sodium salt), lower alkyl p-hydroxybenzoates, chlorhexidine (for example in the form of the acetate or gluconate) and phenyl mercury borate. Other suitable preservatives are: pharmaceutically useful quaternary ammonium compounds, for example cetylpyridinium chloride, tetradecyltrimethyl ammonium bromide, generally known as "cetrimide", benzyldimethyl-[2-[2-[p-(1,1,3,3-tetramethyl-butyl)phenoxy]ethoxy]-ammonium chloride, generally known as "benzethonium chloride" and myristyl picolinium chloride. Each of these compounds may be used in a concentration of 0.002 to 0.05%, for example 0.02% (weight/volume in liquid formulations, otherwise weight/weight). Preferred preservatives among the quaternary ammonium compounds are, however, alkylbenzyl dimethyl ammonium chloride and mixtures thereof for example the compounds generally known as "benzalkonium chloride".

The total amount of preservatives in the formulations (solutions, ointments, etc.) is preferably from 0.001 to 0.10 g, preferably 0.01 g per 100 ml of solution/suspension or 100 g of formulation.

In the case of preservatives, the following amounts of individual substances can, for example, be used: thimero sal 0.002-0.02%; benzalkonium chloride 0.002 to 0.02% (in combination with thimero sal the amount of thimero sal is, for example=0.002 to 0.005%;); chlorhexidine acetate or gluconate 0.01 to 0.02%; phenyl mercuric/nitrate, borate, acetate 0.002-0.004%; p-hydroxybenzoic acid ester (for example, a mixture of the methyl ester and propyl ester in the ratio 7:3): preferably 0.05-0.15, more preferably 0.1%.

The preservative used is preferably a combination of edetic acid (for example, as the disodium salt) and benzalkonium chloride. In this combination, the edetic acid is preferably used in a concentration of 0.05 to 0.1%, benzalkonium chloride preferably being used in a concentration of 0.005 to 0.05%, more preferably 0.01%.

In the case of solutions/suspensions reference is always made to percent by weight/volume, in the case of solid or semi-solid formulations to percent by weight/weight of the formulation.

Further auxiliary substances which may, for example, be used for the formulations of the invention are: polyvinyl pyrrolidone, sorbitan fatty acid esters such as sorbitan trioleate, polyethoxylated sorbitan fatty acid esters (for example polyethoxylated sorbitan trioleate), sorbimacrogol oleate, synthetic amphotensides (tritons), ethylene oxide ethers of octylphenolformaldehyde condensation products, phosphatides such as lecithin, polyethoxylated fats, polyethoxylated oleotriglycerides and polyethoxylated fatty alcohols. In this context, polyethoxylated means that the relevant substances contain polyoxyethylene chains, the degree of polymerisation of which is generally between 2 to 40, in particular between 10 to 20. These substances are preferably used to improve the solubility of the azelastine component.

It is optionally possible to use additional isotonization agents. Isotonization agents which may, for example, be used are: saccharose, glucose, glycerine, sorbitol, 1,2-propylene glycol and NaCl.

The isotonization agents adjust the osmotic pressure of the formulations to the same osmotic pressure as nasal secretion For this purpose these substances are in each case to be used in such amount that, for example, in the case of a solution, a reduction in the freezing point of 0.50 to 0.56 degree C. is attained in comparison to pure water.

In Example 1, it is possible to use instead of NaCl per 100 ml of solution, for example: Glucose $1H_2O$ 3.81 g; saccharose 6.35 g; glycerine 2.2 g; 1,2-propylene glycol 1.617 g; sorbitol 3.84 g (in the case of mixtures of these substances correspondingly less may optionally be used).

Moreover, it is possible to add thickening agents to solutions according to the present invention to prevent the solution from flowing out of the nose too quickly and to give the solution a viscosity of about 1.5 to 3, preferably 2 mPa.

Such thickening agents may, for example, be: cellulose derivatives (for example cellulose ether) in which the cellulose-hydroxy groups are partially etherified with lower unsaturated aliphatic alcohols and/or lower unsaturated aliphatic oxyalcohols (for example methyl cellulose, carboxymethyl cellulose, hydroxypropyhnethylcellulose), gelatin, polyvinylpyrrolidone, tragacanth, ethoxose (water soluble binding and thickening agents on the basis of ethyl cellulose), alginic acid, polyvinyl alcohol, polyacrylic acid, pectin and equivalent agents. Should these substances contain acid groups, the corresponding physiologically acceptable salts may also be used.

In the event of the use of hydroxypropyl cellulose, 0.1% by weight of the formulation, for example, is used for this purpose.

In the event of the use of Avicel RC 591 or CL 611, microcrystalline cellulose and carboxymethyl cellulose sodium commercially available from FMC BioPolymer, 0.65-3.0% by weight of the formulation, for example, is used for the purpose.

It is also possible to add to the formulations buffer substances such as citric acid/sodium hydrogensulphate borate buffer, phosphates (sodium hydrogenorthophosphate, disodium hydrogenphosphate), trometamol or equivalent conventional buffers in order, for example, to adjust the formulations to a pH value of 3 to 7, preferably 4.5 to 6.5.

The amount of citric acid is, for example, 0.01 to 0.14 g, preferably 0.04 to 0.05 g, the amount of disodium hydrogenphosphate 0.1 to 0.5 g, preferably 0.2 to 0.3 g per 100 ml of solution. The weights given relate in each case to the anhydrous substances.

In the case of solutions and suspensions, the maximum total concentration of active agent and buffer is preferably less than 5%, in particular less than 2% (weight/volume).

For the nasal application, a solution or suspension can preferably be used which is applied as an aerosol, i.e. in the form of a fine dispersion in air or in another conventional carrier gas, for example by means of a conventional pump vaporizer.

Application as a dosage aerosol is, however, also possible. Dosage aerosols are defined as being pressure packings which contain the azelastine or its salts in combination with steroid, in the form of a solution or suspension in a so-called propellant. The propellant may be a pressurized liquid chlorinated, fluorinated hydrocarbon or mixtures of various chlorinated, fluorinated hydrocarbons as well as propane, butane, isobutene or mixtures of these among themselves or with chlorinated, fluorinated hydrocarbons which are gaseous at atmospheric pressure and room temperature. Hydrofluorocarbons (HFCs), such as HFC 134a, and HFC 227a can also be used, and are preferred for environmental reasons. The pressure packing has a dosage or metering valve which, on actuation, releases a defined amount of the solution or suspension of the medicament. The subsequent very sudden vaporization of the propellant tears the solution or suspension of azelastine into the finest droplets or minute particles which can be sprayed in the nose or which are available for inspiration into the nose. Certain plastic applicators may be used to actuate the valve and to convey the sprayed suspension into the nose.

In the case of application as an aerosol, it is also possible to use a conventional adapter.

Particularly preferred embodiments of the present invention are hereinafter described and it will of course be appreciated that any of the previous description of suitable ingredients and formulation characteristics can also be applicable to the following products and formulations as provided by the present invention.

It will be appreciated, therefore, that the present invention further provides a pharmaceutical product comprising (i) azelastine, or a pharmaceutically acceptable salt, solvate or physiologically functional derivative thereof, provided in an aerosol formulation preferably together with a propellant typically suitable for MDI delivery, and (ii) at least one steroid, or a pharmaceutically acceptable salt, solvate or physiologically functional derivative thereof, provided in an aerosol formulation preferably together with a propellant typically suitable for MDI delivery, as a combined preparation for simultaneous, separate or sequential use in the treatment of conditions for which administration of one or more anti-histamine and/or one or more steroid is indicated.

The present invention also provides an aerosol formulation preferably suitable for MDI delivery comprising (i) azelastine, or a pharmaceutically acceptable salt, solvate or physiologically functional derivative thereof and (ii) at least one steroid, or a pharmaceutically acceptable salt, solvate or physiologically functional derivative thereof, together with a propellant.

It will also be appreciated from the above, that the respective therapeutic agents of the combined preparation can be administered simultaneously, either in the same or different pharmaceutical formulations, or separately or sequentially. If there is separate or sequential administration, it will also be appreciated that the subsequently administered therapeutic agents should be administered to a patient within a time scale so as to achieve, or more particularly optimise, the above referred to advantageous synergistic therapeutic effect of a combined preparation as present in a pharmaceutical product according to the present invention.

Suitable propellants for use in pharmaceutical products of formulations as provided by the present invention include 1,1,1,2-tetrafluoroethane (HFA 134a) or 1,1,1,2,3,3,3,-heptafluoropropane (HFA 227), or a combination of both, or mono-fluoro trichloromethane and dichloro difluoromethane, in particular 1,1,1,2-tetrafluoroethane (HFA 134a) or 1,1,1,2,3,3,3-heptafluoropropane (HFA 227), with HFA 134a being preferred.

A pharmaceutical aerosol formulation according to the present invention preferably further comprises a polar cosolvent such as $C_{2-6}$ aliphatic alcohols and polyols, for example ethanol, isopropanol and propylene glycol, with ethanol often being preferred. Preferably, the concentration of the cosolvent is in the range of about 2 to 10% by weight, typically up to about 5%, of the total formulation.

A pharmaceutical aerosol formulation according to the present invention may further comprise one or more surfactants. Such surfactants can be included to stabilise the formulations and for lubrication of a valve system. Some of the most commonly used surfactants in aerosol formulations are oils derived from natural sources, such as corn oil, olive oil, cottonseed oil and sunflower seed oil, and also phospholipids. Suitable surfactants can include lecithin, oleic acid or sorbitan oleate. In an embodiment, the formulation contains from about 50 micrograms to about 1 milligram of surfactant per ml of the formulation.

A further preferred embodiment of the present invention can be where a formulation or product is provided in the form of insufflatable powder, where preferably the maximum particle size of the substance suitably does not exceed 10 µm. Azelastine or its salts and the steroid may be mixed with inert carrier substances or drawn up onto inert carrier substances. Carrier substances which may, for example, be used are: sugars such as glucose, saccharose, lactose and fructose. Also starches or starch derivatives, oligosaccharides such as dextrins, cyclodextrins and their derivatives, polyvinylpyrrolidone, alginic acid, tylose, silicic acid, cellulose, cellulose derivatives (for example cellulose ether), sugar alcohols such as mannitol or sorbitol, calcium carbonate, calcium phosphate, etc.

In one embodiment, the therapeutic agents employed have a particle size of less than about 10 µm, preferably less than 5 µm.

The use of insufflation powders can represent a preferred embodiment of the present invention and there is provided by the present invention a pharmaceutical product comprising (i) azelastine, or a pharmaceutically acceptable salt, solvate or physiologically functional derivative thereof, provided as an insufflation powder, and (ii) at least one steroid, or a pharmaceutically acceptable salt, solvate or physiologically functional derivative thereof, provided as an insufflation powder, as a combined preparation for simultaneous, separate or sequential use in the treatment of conditions for which administration of one or more anti-histamine and/or one or more steroid is indicated.

It will be appreciated from the above, that the respective therapeutic agents of the combined preparation can be administered simultaneously, either in the same or different insufflation powder formulations, or separately or sequentially. If there is separate or sequential administration as discussed above, it will also be appreciated that the subsequently administered therapeutic agents should be administered to a patient within a time scale so as to achieve, or more particularly optimise, the above referred to advantageous synergistic therapeutic effect of a combined preparation as present in a pharmaceutical product according to the present invention.

The present invention also provides an insufflation powder formulation comprising (i) azelastine, or a pharmaceutically acceptable salt, solvate or physiologically functional derivative thereof, and (ii) at least one steroid, or a pharmaceutically acceptable salt, solvate or physiologically functional derivative thereof, together with a pharmaceutically acceptable carrier or excipient therefor.

Dry insufflation powder formulations as provided by the present invention can be beneficial where it is required that therapeutic agents as employed according to the present invention are retained in the nasal cavity, and systemic side effects can be minimised or eliminated. Furthermore, insufflation powder formulations as employed in the present invention can be beneficial whereby retention of azelastine, or a pharmaceutically acceptable salt, solvate or physiologically functional derivative thereof, at the nasal mucosa is improved, and the bitter aftertaste associated with liquid antihistamine formulations significantly reduced, whilst also exhibiting the synergistic therapeutic effect associated with the azelastine/steroid combinations provided by the present invention. By providing a dry insufflation powder formulation of azelastine, together with a steroid, having an average particle size of less than about 10 µm, the therapeutic agents can be restricted primarily to the desired target organ, the nasal mucosa.

A dry powder insufflation formulation according to the present invention can be administered by the use of an insufflator, which can produce a finely divided cloud of the dry powder. The insufflator preferably is provided with means to ensure administration of a substantially pre-determined amount of a formulation or product as provided by the present invention The powder may be used directly with an insufflator which is provided with a bottle or container for the powder, or the powder may be filled into a capsule or cartridge, such as a gelatin capsule, or other single dose device adapted for administration. The insufflator preferably has means to open the capsule or other dose device.

Preferred combinations of therapeutic agents employed in pharmaceutical products and formulations according to the present invention (in particular nasal sprays or drops, aerosol or insulation products and formulations as described above) comprise any one of the following combinations.

The present invention further provides, therefore, a pharmaceutical product comprising (i) azelastine, or a pharmaceutically acceptable salt thereof, and (ii) at least one steroid selected from the group consisting of beclomethasone, fluticasone, mometasone and pharmaceutically acceptable esters thereof, as a combined preparation for simultaneous, separate or sequential use in the treatment of conditions for which administration of one or more anti-histamine and/or one or more steroid is indicated Suitably the esters can be selected from beclomethasone dipropionate, fluticasone propionate, fluticasone valerate, mometasone furoate and mometasone furoate monohydrate.

The present invention also provides a pharmaceutical formulation comprising (i) azelastine, or a pharmaceutically acceptable salt thereof, and (ii) at least one steroid selected from the group consisting of beclomethasone, fluticasone, mometasone and pharmaceutically acceptable esters thereof together with a pharmaceutically acceptable carrier or excipient therefor. Suitably the esters can be selected from beclomethasone dipropionate, fluticasone propionate, fluticasone valerate, mometasone furoate and mometasone furoate monohydrate.

In the case of a nasal spray, a particularly preferred formulation as provided by the present invention is a nasal spray comprising azelastine, or a pharmaceutically acceptable salt thereof (preferably azelastine hydrochloride), together with mometasone either as the free base or in ester form, preferably as mometasone furoate.

Specific combinations of therapeutic agents employed in pharmaceutical products and formulations according to the present invention comprise any one of the following combinations:

azelastine hydrochloride and beclomethasone dipropionate;
azelastine hydrochloride and fluticasone propionate;
azelastine hydrochloride and fluticasone valerate;
azelastine hydrochloride and mometasone furoate; and
azelastine hydrochloride and mometasone furoate monohydrate.

There is also provided by the present invention a method for the prophylaxis or treatment in a mammal, such as a human, of conditions for which administration of one or more anti-histamine and/or one or more steroid is indicated, which method comprises administration of a therapeutically effective amount of a pharmaceutical product substantially as hereinbefore described, as a combined preparation for simultaneous, separate or sequential use in the treatment of such conditions.

The present invention also provides a method for the prophylaxis or treatment in a mammal, such as a human, of conditions for which administration of one or more anti-histamine and/or one or more steroid is indicated, which method comprises administration of a therapeutically effective amount of a pharmaceutical formulation substantially as hereinbefore described.

There is also provided by the present invention for use in the manufacture of a medicament for the prophylaxis or treatment in a mammal, such as a human, of conditions for which administration of one or more anti-histamine and/or one or more steroid is indicated, a pharmaceutical product, as a combined preparation for simultaneous, separate or sequential use in the treatment of such conditions.

There is further provided by the present invention, therefore, a process of preparing a pharmaceutical product substantially as hereinbefore described, which process comprises providing as a combined preparation for simultaneous, separate or sequential use in the treatment of conditions for which administration of one or more anti-histamine and/or one or more steroid is indicated: (i) azelastine, or a pharmaceutically acceptable salt, solvate or physiologically functional derivative thereof, and (ii) at least one steroid, or a pharmaceutically acceptable salt, solvate or physiologically functional derivative thereof.

The present invention also provides a process of preparing a pharmaceutical formulation substantially as hereinbefore described, which process comprises admixing a pharmaceutically acceptable carrier or excipient with: (i) azelastine, or a pharmaceutically acceptable salt, solvate or physiologically functional derivative thereof, and (ii) at least one steroid, or a pharmaceutically acceptable salt, solvate or physiologically functional derivative thereof Preferably pharmaceutical formulations according to the present invention can comprise insufflation powder formulations, nasal sprays, nasal inhalation solutions or aerosols substantially as hereinbefore described.

The present invention is now illustrated by the following Examples, which do not limit the scope of the invention in any way. In Examples where only the ingredients of formulations according to the present invention are listed, these formulations are prepared by techniques well known in the art.

EXAMPLE 1

Nasal Spray or Nasal Drops with 0.1% Azelastine Hydrochloride as Active Ingredient and Steroid 0.1%

| Sr. No | Ingredients | Quantity % w/v |
|---|---|---|
| 1. | Azelastine hydrochloride | 0.1% |
| 2. | Steroid | 0.1% |
| 3. | Disodium edetate | 0.005% |
| 4. | Sodium chloride | 0.9% |
| 5. | Benzalkonium chloride | 0.001% |
| 6. | Avicel RC 591 | 1.2% |
| 7. | Citric acid monohydrate | 0.2% |
| 8. | Disodium hydrogen phosphate dodecahydrate | 0.1% |
| 9. | Purified water | |

EXAMPLE 2

Dosage aerosol giving off 0.5 mg of azelastine hydrochloride and 50 micrograms of beclomethasone dipropionate freon solvate per stroke.

About 8.0 kg of a mixture of 70 parts by weight of difluorodichloromethane and 30 parts by weight of 1,2dichlorotetrafluoroethane are cooled to about −55 degree C. in an appropriate cooling vessel. A mixture of 0.086 kg of pre-cooled sorbitantrioleate and 0.8600 kg of pre-cooled trichlorofluoromethane are dissolved with stirring into the mixture at −55 degrees C., 0.0688 kg of micronized azelastine hydrochloride, 0.00688 kg of beclomethasone dipropionate freon solvate and 0.0688 kg of micronized lactose are then incorporated in portions into the solution thereby obtained with intensive stirring. The total weight of the suspension thereby obtained is made up to 9.547 kg through addition of more of the mixture of 70 parts by weight of difluorodichloromethane and 30 parts by weight of 1,2-dichlorotetrafluoroethane cooled to about −55 degree C.

Following closure of the cooling vessel the suspension is again cooled to about −55 degrees C. under intensive stirring. It is then ready to be filled.

EXAMPLE 3

Nasal Spray or Nasal Drops with Azelastine and Steroid*

| Sr. No. | Ingredients | Quantity (% w/w) |
|---|---|---|
| | Azelastine Hydrochloride | 0.10 |
| | Fluticasone propionate | 0.0357 |
| | Glycerin | 2.60 |
| | Avicel RC 591 | 1.35 |
| | Polysorbate 80 | 0.025 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone propionate (50 mcg).

EXAMPLE 4

Nasal Spray or Nasal Drops with Azelastine and Steroid*

| Sr. No. | Ingredients | Quantity (% w/w) |
|---|---|---|
| | Azelastine Hydrochloride | 0.10 |
| | Fluticasone valerate | 0.0357 |
| | Glycerin | 2.60 |
| | Avicel RC 591 | 1.20 |
| | Polysorbate 80 | 0.030 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone valerate (50 mcg).

EXAMPLE 5

Nasal Spray or Nasal Drops with Azelastine and Steroid*

| Sr. No. | Ingredients | Quantity (% w/w) |
|---|---|---|
| | Azelastine Hydrochloride | 0.10 |
| | Fluticasone propionate | 0.0714 |
| | Glycerin | 2.60 |
| | Avicel RC 581 | 1.35 |
| | Polysorbate 80 | 0.025 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone propionate (50 mcg).

EXAMPLE 6

Nasal Spray or Nasal Drops with Azelastine and Steroid

| Sr. No. | Ingredients | Quantity (% w/w) |
|---|---|---|
| | Azelastine Hydrochloride | 0.10 |
| | Mometasone Furoate | 0.05173 |
| | Glycerin | 2.30 |
| | Disodium edetate | 0.005 |
| | Polysorbate 80 | 0.0125 |
| | Avicel RC 581 | 1.35 |
| | Benzalkonium chloride | 0.01 |
| | Citric acid monohydrate | 0.20 |
| | Disodium hydrogen phosphate dodecahydrate | 0.10 |
| | Purified water | q.s. |

EXAMPLE 7

Nasal Spray or Nasal Drops with Azelastine and Steroid*

| Sr. No. | Ingredients | Quantity (% w/w) |
|---|---|---|
| | Azelastine Hydrochloride | 0.10 |
| | Mometasone Furoate monohydrate | 0.05173 |
| | Glycerin | 2.60 |
| | Avicel CL 611 | 2.295 |
| | Polysorbate 80 | 0.0125 |
| | Benzalkonium chloride | 0.01 |
| | Phenyl ethyl alcohol | 0.25 |
| | Purified water | q.s. |

*Each spray delivers Azelastine Hydrochloride (140 mcg) and Mometasone furoate (50 mcg).

EXAMPLE 8

Nasal MDI with Azelastine and Steroid

| Sr. No. | Ingredients | Quantity in mcg |
|---|---|---|
| | Azelastine Hydrochloride | 140 |
| | Mometasone Furoate monohydrate | 50 |
| | HFA 134a | q.s. |
| | Lecithin | 0.1% |
| | Alcohol | (up to 5%) |

EXAMPLE 9

Nasal MDI with Azelastine and Steroid

| Sr. No. | Ingredients | Quantity in mcg |
|---|---|---|
| | Azelastine Hydrochloride | 140 |
| | Fluticasone propionate | 50 |
| | HFA 134a | q.s. |
| | Sorbitan trioleate | 0.1% |
| | Alcohol | (up to 5%) |

EXAMPLE 10

Nasal MDI with Azelastine and Steroid

| Sr. No. | Ingredients | Quantity in mcg |
|---|---|---|
| | Azelastine Hydrochloride | 140 |
| | Fluticasone propionate | 100 |
| | HFA 134a | q.s. |
| | Oleic acid | 0.1% |

EXAMPLE 11

Nasal MDI with Azelastine and Steroid

| Sr. No. | Ingredients | Quantity in mcg |
|---|---|---|
| | Azelastine Hydrochloride | 140 |
| | Fluticasone Valerate | 50 |
| | HFA 134a | q.s. |
| | Alcohol | (up to 5%) |

Insufflatable Powders Containing Azelastine and Steroid:

| Sr. No. | Ingredients | Quantity (% w/w) |
|---|---|---|
| | Azelastine Hydrochloride (Micronized) | 140 mcg |
| | Fluticasone propionate | 50 mcg |
| | Lactose | q.s. (up to 25 mcg) |

| Sr. No. | Ingredients | Quantity (% w/w) |
|---|---|---|
| | Azelastine Hydrochloride (Micronized) | 140 mcg |
| | Fluticasone propionate | 100 mcg |
| | Mannitol | q.s. (up to 30 mcg) |

| Sr. No. | Ingredients | Quantity (% w/w) |
|---|---|---|
| | Azelastine Hydrochloride (Micronized) | 140 mcg |
| | Fluticasone propionate | 250 mcg |
| | Lactose | q.s. (up to 30 mcg) |

The invention claimed is:

1. A pharmaceutical formulation comprising:
   azelastine, or a pharmaceutically acceptable salt thereof, and
   a pharmaceutically acceptable ester of fluticasone,
   wherein said pharmaceutical formulation is in a dosage form suitable for nasal administration.

2. The pharmaceutical formulation of claim 1, wherein said pharmaceutically acceptable salt of azelastine is azelastine hydrochloride.

3. The pharmaceutical formulation of claim 1, wherein said pharmaceutically acceptable ester of fluticasone is fluticasone propionate or fluticasone valerate.

4. The pharmaceutical formulation of claim 1, wherein said formulation has a particle size of less than 10 μm.

5. The pharmaceutical formulation of claim 1, wherein said formulation is an aqueous suspension comprising from 0.0005% (weight/weight) to 2% (weight/weight) of said azelastine, or said pharmaceutically acceptable salt thereof, and from 0.0357% (weight/weight) to 1.5% (weight/weight) of said pharmaceutically acceptable ester of fluticasone.

6. The pharmaceutical formulation according to claim 5, comprising from 0.001% (weight/weight) to 1% (weight/weight) of said azelastine, or said pharmaceutically acceptable salt thereof, and from 0.0357% (weight/weight) to 1.5% (weight/weight) of said pharmaceutically acceptable ester of fluticasone.

7. The pharmaceutical formulation of claim 1, further comprising at least one additive selected from the group consisting of a buffer, a preservative, a suspending agent a thickening agent, a surfactant, an isotonic agent and combinations thereof.

8. The pharmaceutical formulation of claim 7, wherein said surfactant comprises a polysorbate, poloxamer or combinations thereof.

9. The pharmaceutical formulation of claim 7, wherein said isotonic agent comprises sodium chloride, saccharose, glucose, glycerine, sorbitol, 1,2-propylene glycol or combinations thereof.

10. The pharmaceutical formulation of claim 7, wherein said preservative comprises edetic acid or its alkali salts, lower alkyl p-hydroxybenzoates, chlorhexidine, phenyl mercury borate, or benzoic acid or a salt thereof, a quaternary ammonium compound, sorbic acid or a salt thereof, or combinations thereof.

11. The pharmaceutical formulation of claim 7, wherein said suspending agent or said thickening agent comprises cellulose derivatives, gelatin, polyvinylpyrrolidone, tragacanth, alginic acid, polyvinyl alcohol, polyacrylic acid, pectin, or combinations thereof.

12. The pharmaceutical formulation of claim 1, which is an aqueous suspension.

13. The pharmaceutical formulation of claim 1, wherein said dosage form suitable for nasal administration comprises nasal drops or a nasal spray.

14. The pharmaceutical formulation of claim 1, wherein said dosage form suitable for nasal administration comprises nasal drops.

15. The pharmaceutical formulation of claim 1, wherein said dosage form suitable for nasal administration comprises a nasal spray.

16. The pharmaceutical formulation of claim 1, wherein said formulation is used in the treatment of conditions for which administration of one or more anti-histamine and/or one or more steroid is indicated.

17. The pharmaceutical formulation of claim 1, wherein said pharmaceutically acceptable salt of azelastine is azelastine hydrochloride and said pharmaceutically acceptable ester of fluticasone is fluticasone propionate, and wherein said formulation is used in the treatment of conditions for which administration of one or more anti-histamine and/or one or more steroid is indicated.

18. The pharmaceutical formulation of claim 1, wherein said pharmaceutically acceptable salt of azelastine is azelastine hydrochloride and said pharmaceutically acceptable ester of fluticasone is fluticasone propionate, and wherein said formulation further comprises a pharmaceutically acceptable carrier or excipient therefor.

19. The pharmaceutical formulation of claim 1, wherein said pharmaceutically acceptable salt of azelastine is azelastine hydrochloride and said pharmaceutically acceptable ester of fluticasone is fluticasone valerate, and wherein said formulation is used in the treatment of conditions for which administration of one or more anti-histamine and/or one or more steroid is indicated.

20. The pharmaceutical formulation of claim 1, wherein said pharmaceutically acceptable salt of azelastine is azelastine hydrochloride and said pharmaceutically acceptable ester of fluticasone is fluticasone valerate, and wherein said formulation further comprises a pharmaceutically acceptable carrier or excipient therefor.

21. A process of preparing a pharmaceutical formulation of claim 1, which process comprises admixing a pharmaceutically acceptable carrier or excipient with azelastine, or a pharmaceutically acceptable salt thereof, and a pharmaceutically acceptable ester of fluticasone.

22. The pharmaceutical formulation of claim 1, wherein said pharmaceutically acceptable ester of fluticasone is fluticasone propionate.

23. The pharmaceutical formulation of claim 1, wherein said pharmaceutically acceptable ester of fluticasone is fluticasone valerate.

24. A pharmaceutical formulation comprising
azelastine hydrochloride; and,
fluticasone propionate,
wherein said formulation is in the dosage form of as a nasal spray, and wherein said formulation is used in the treatment of conditions for which administration of one or more anti-histamine and/or one or more steroid is indicated.

25. A nasal spray formulation comprising (i) azelastine, or a pharmaceutically acceptable salt thereof, (ii) a pharmaceutically acceptable ester of fluticasone, and (iii) a pharmaceutically acceptable carrier or excipient therefor.

26. The pharmaceutical formulation of claim 6, comprising 0.1% (weight/weight) of azelastine hydrochloride, and from 0.0357% to 1.5% (weight/weight) of fluticasone propionate.

27. The pharmaceutical formulation of claim 6, comprising 0.1% (weight/weight) of azelastine hydrochloride, and from 0.0357% to 1.5% (weight/weight) of fluticasone valerate.

28. The pharmaceutical formulation of claim 6, wherein said dosage form suitable for nasal administration comprises a nasal spray.

29. The pharmaceutical formulation of claim 26, wherein said dosage form suitable for nasal administration comprises a nasal spray.

30. The pharmaceutical formulation of claim 27, wherein said dosage form suitable for nasal administration comprises a nasal spray.

31. The pharmaceutical formulation of claim 28, wherein said pharmaceutically acceptable salt of azelastine is azelastine hydrochloride and wherein said pharmaceutically acceptable ester of fluticasone is fluticasone propionate.

32. The pharmaceutical formulation of claim 28, wherein said pharmaceutically acceptable salt of azelastine is azelastine hydrochloride and wherein said pharmaceutically acceptable ester of fluticasone is fluticasone valerate.

33. The pharmaceutical formulation of claim 25, wherein said pharmaceutically acceptable salt of azelastine is azelastine hydrochloride and wherein said pharmaceutically acceptable ester of fluticasone is fluticasone propionate.

34. The pharmaceutical formulation of claim 25, wherein said pharmaceutically acceptable salt of azelastine is azelastine hydrochloride and wherein said pharmaceutically acceptable ester of fluticasone is fluticasone valerate.

35. The pharmaceutical formulation of claim 5, wherein said pharmaceutically acceptable salt of azelastine is azelastine hydrochloride.

36. The pharmaceutical formulation of claim 6, wherein said pharmaceutically acceptable salt of azelastine is azelastine hydrochloride.

37. The pharmaceutical formulation of claim 28, wherein said pharmaceutically acceptable salt of azelastine is azelastine hydrochloride.

38. The pharmaceutical formulation of claim 8, wherein said surfactant comprises a polysorbate.

39. The pharmaceutical formulation of claim 9, wherein said isotonic agent comprises glycerine.

40. The pharmaceutical formulation of claim 10, wherein said preservative comprises edetate disodium and benzalkonium chloride.

41. The pharmaceutical formulation of claim 11, wherein said suspending agent or said thickening agent comprises cellulose derivatives.

42. The pharmaceutical formulation of claim 1, further comprising edetate disodium, glycerine, a thickening agent comprising microcrystalline cellulose and sodium carboxy methyl cellulose, polysorbate 80, benzalkonium chloride, phenyl ethyl alcohol, and purified water.

43. The pharmaceutical formulation of claim 24, further comprising edetate disodium, glycerine, a thickening agent comprising microcrystalline cellulose and sodium carboxy methyl cellulose, polysorbate 80, benzalkonium chloride, phenyl ethyl alcohol, and purified water.

44. The pharmaceutical formulation of claim 25, further comprising edetate disodium, glycerine, a thickening agent comprising microcrystalline cellulose and sodium carboxy methyl cellulose, polysorbate 80, benzalkonium chloride, phenyl ethyl alcohol, and purified water.

45. The pharmaceutical formulation of claim 1, wherein said formulation comprises a pH from 3 to 7.

46. The pharmaceutical formulation of claim 1, wherein said formulation comprises a pH from 4.5 to 6.5.

47. A pharmaceutical formulation comprising from 0.001% (weight/weight) to 1% (weight/weight) of azelastine hydrochloride, and from 0.0357% (weight/weight) to 1.5% (weight/weight) of fluticasone propionate, wherein said pharmaceutical formulation is an aqueous suspension suitable for nasal administration.

48. A pharmaceutical formulation comprising 1% (weight/weight) of azelastine hydrochloride, and from 0.0357% (weight/weight) to 1.5% (weight/weight) of fluticasone propionate, wherein said pharmaceutical formulation is an aqueous suspension suitable for nasal administration.

* * * * *

UNITED STATES PATENT AND TRADEMARK OFFICE
CERTIFICATE OF CORRECTION

PATENT NO.        : 8,168,620 B2
APPLICATION NO.   : 10/518016
DATED             : May 1, 2012
INVENTOR(S)       : Amar Lulla et al.

It is certified that error appears in the above-identified patent and that said Letters Patent is hereby corrected as shown below:

In the claims:

Column 12, Claim 7, Line 7; Replace: "a suspending agent a thickening agent" with --a suspending agent, a thickening agent--
Column 12, Claim 10, Lines 20-21; Replace: "phenyl mercury borate, or benzoic acid" with --phenyl mercury borate, benzoic acid--
Column 13, Claim 24, Lines 19-20; Replace: "dosage form of as a nasal spray" with --dosage form of a nasal spray--

Signed and Sealed this
Eighteenth Day of November, 2014

Michelle K. Lee
*Deputy Director of the United States Patent and Trademark Office*